(12) United States Patent
Alberte, Jr. et al.

(10) Patent No.: US 8,696,565 B2
(45) Date of Patent: Apr. 15, 2014

(54) PATIENT MONITORING SYSTEM WITH HEALTH STATUS INDICATOR

(75) Inventors: Robert Joseph Alberte, Jr., Oconomowoc, WI (US); Carl Claude Davis, Menomonee Falls, WI (US); David Alan Sitzman, Hubertus, WI (US)

(73) Assignee: General Electric Company, Schenectady, NY (US)

(*) Notice: Subject to any disclaimer, the term of this patent is extended or adjusted under 35 U.S.C. 154(b) by 1030 days.

(21) Appl. No.: 12/132,062

(22) Filed: Jun. 3, 2008

(65) Prior Publication Data
US 2009/0299150 A1    Dec. 3, 2009

(51) Int. Cl.
*A61B 5/00*    (2006.01)
*G06F 19/00*    (2011.01)
*G06T 11/00*    (2006.01)

(52) U.S. Cl.
CPC ........ *G06F 19/3406* (2013.01); *G06F 19/3431* (2013.01); *G06F 19/345* (2013.01); *G06F 19/30* (2013.01); *G06F 19/3487* (2013.01); *G06T 11/00* (2013.01); *G06T 11/001* (2013.01); *A61B 5/00* (2013.01); *A61B 5/74* (2013.01); *A61B 5/7445* (2013.01); *A61B 5/4842* (2013.01); *G06T 2210/41* (2013.01); *Y10S 128/92* (2013.01)
USPC ........... 600/300; 600/301; 715/700; 345/582; 345/589; 345/619; 345/440; 345/440.1; 128/920

(58) Field of Classification Search
USPC ......... 600/300–301, 509, 500, 529, 365, 485, 600/549; 128/920–925; 715/700; 345/428, 345/581–618, 440, 440.1, 440.2, 441–443
See application file for complete search history.

(56) References Cited

U.S. PATENT DOCUMENTS

| | | | | |
|---|---|---|---|---|
| 5,262,944 A | * | 11/1993 | Weisner et al. | 600/300 |
| 5,473,536 A | * | 12/1995 | Wimmer | 700/90 |
| 5,838,938 A | | 11/1998 | Morgan | |
| 5,899,855 A | | 5/1999 | Brown | |
| 6,292,184 B1 | | 9/2001 | Morgan | |
| 7,038,588 B2 | * | 5/2006 | Boone et al. | 340/573.1 |

(Continued)

FOREIGN PATENT DOCUMENTS

| | | |
|---|---|---|
| EP | 1054338 | 11/2000 |
| GB | 2438757 | 12/2007 |

(Continued)

OTHER PUBLICATIONS

Unofficial translation of Japanese Office Action from JP Application No. 2009-129762 dated Sep. 24, 2013.

(Continued)

*Primary Examiner* — Bill Thomson
*Assistant Examiner* — Marie Archer
(74) *Attorney, Agent, or Firm* — Andrus Intellectual Property Law, LLP

(57) ABSTRACT

A patient monitoring system is disclosed herein. The patient monitoring system includes a computer adapted to assess the health of a patient, and to generate a health status indicator for the patient. The health status indicator comprising a visual gradient adapted to visually convey the assessed health of the patient. The system also includes a display operatively connected to the computer. The display is configured to display the health status indicator comprising the visual gradient.

11 Claims, 2 Drawing Sheets

(56) References Cited

U.S. PATENT DOCUMENTS

| | | | |
|---|---|---|---|
| 7,311,666 B2* | 12/2007 | Stupp et al. | 600/300 |
| 7,371,214 B2 | 5/2008 | Kouchi et al. | |
| 2003/0117296 A1* | 6/2003 | Seely | 340/870.07 |
| 2004/0119712 A1* | 6/2004 | Kenknight et al. | 345/440 |
| 2005/0203360 A1* | 9/2005 | Brauker et al. | 600/345 |
| 2005/0213125 A1* | 9/2005 | Smith et al. | 358/1.9 |
| 2005/0270302 A1* | 12/2005 | Weast | 345/590 |
| 2006/0200009 A1* | 9/2006 | Wekell et al. | 600/300 |
| 2007/0142716 A1 | 6/2007 | Biondi | |
| 2007/0182755 A1* | 8/2007 | Jones et al. | 345/592 |
| 2008/0055074 A1 | 3/2008 | Gao et al. | |
| 2009/0046096 A1* | 2/2009 | Rampersad | 345/419 |

FOREIGN PATENT DOCUMENTS

| | | |
|---|---|---|
| JP | 05312053 B2 | 10/2013 |
| WO | WO0193241 | 12/2001 |
| WO | 2004-019779 A1 | 3/2004 |
| WO | WO2005087091 | 9/2005 |
| WO | WO 2006094055 A2 * | 9/2006 |
| WO | 2007/101343 A1 | 9/2007 |
| WO | WO03091838 | 11/2009 |

OTHER PUBLICATIONS

JP Application 2009-129762 Office Action.
JP Office Action Translation.

* cited by examiner

PATIENT MONITORING SYSTEM WITH HEALTH STATUS INDICATOR

BACKGROUND OF THE INVENTION

The subject matter disclosed herein relates to a patient monitoring system with a health status indicator.

Multi-patient displays enable a single technician to generally simultaneously monitor a plurality of patients. Multi-patient displays are commonly implemented in centralized patient monitoring systems wherein a plurality of technicians collectively monitor a large number of patients from a single location, and in hallway display systems wherein patient data pertaining to a plurality of different patients is visually conveyed in a hospital hallway.

Some conventional multi-patient displays are configured to enable a single technician to monitor as many as 96 patients. One problem with such conventional multi-patient displays is that it can be difficult to efficiently evaluate all the displayed information and identify those specific patients requiring attention.

BRIEF DESCRIPTION OF THE INVENTION

The above-mentioned shortcomings, disadvantages and problems are addressed herein which will be understood by reading and understanding the following specification.

In an embodiment, a system includes a computer adapted to assess the health of a patient, and to generate a health status indicator for the patient. The health status indicator comprising a visual gradient adapted to visually convey the assessed health of the patient. The system also includes a display operatively connected to the computer. The display is configured to display the health status indicator comprising the visual gradient.

In another embodiment, a patient monitoring system includes a computer adapted to generate a health status indicator for each of a plurality of patients. The health status indicator includes a color gradient configured to visually convey a patient health assessment with a variable range of color saturation and/or intensity. The patient monitoring system also includes a multi-patient display operatively connected to the computer. The multi-patient display is configured to generally simultaneously display the health status indicator for each of the patients.

In another embodiment, a method includes obtaining patient data from each of a plurality of patients. The method also includes implementing a computer to assess the health of each of the patients based on the patient data, and to generate a health status indicator for each of the patients. The health status indicator is configured to visually convey the health assessment with a variable range of color saturation and/or intensity. The method also includes generally simultaneously displaying the health status indicator for each of the patients.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
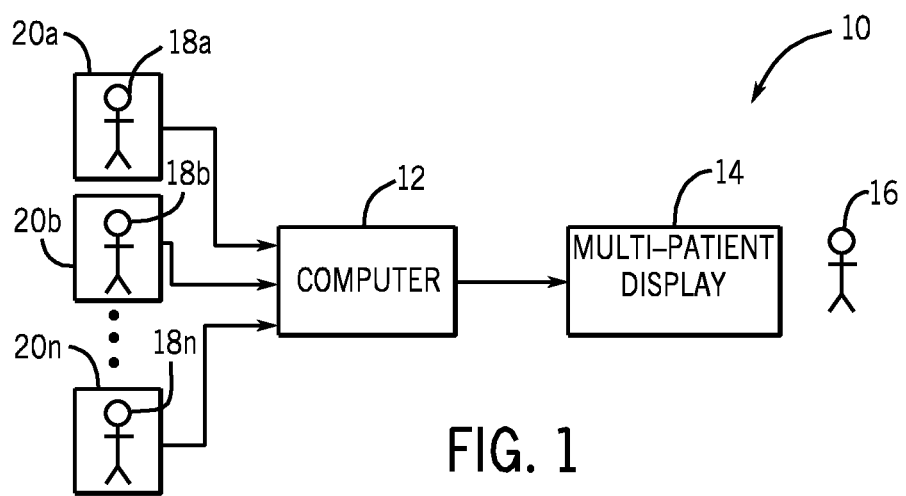
FIG. 1 is a schematic representation of a centralized patient monitoring system in accordance with an embodiment.

Referring to FIG. 1, a patient monitoring system 10 is shown in accordance with one embodiment. The patient monitoring system 10 includes a computer 12 and a display 14. The patient monitoring system 10 will hereinafter be described in accordance with an embodiment as a centralized patient monitoring system 10 adapted to enable a single technician 16 to generally simultaneously monitor a plurality of patients 18a-18n, however, it should be appreciated that other monitoring systems may be envisioned. Similarly, the display 14 will hereinafter be described in accordance with an embodiment as a multi-patient display 14, however, other display types may also be envisioned. According to one alternate embodiment, the display 14 may comprise a single-patient display.

The computer 12 is connected to a plurality of discrete patient monitoring systems 20a-20n. The discrete patient monitoring systems 20a-20n are each configured to monitor one of the patients 18a-18n, to generate patient data based on the specific characteristics being monitored, and to transmit the patient data to the computer 12. In a non-limiting manner, the discrete patient monitoring systems 20a-20n may each comprise an electrocardiograph, a blood pressure monitor, a thermometer, and/or a pulse oximeter. Correspondingly, the patient data generated by the patient monitoring systems 20a-20n may comprise electrocardiogram (ECG) data, blood pressure data, temperature data, and/or pulse data.

The computer 12 is configured to evaluate the patient data from the patient monitoring systems 20a-20n in order assess each patient's health. In a non-limiting manner, the computer 12 may be configured to assess patient health by analyzing the magnitude of the patient data and/or the data's rate of change. As an example, heart rate data falling below a first predetermined value may indicate moderate patient health and the need for attention in the near future, whereas heart rata data falling below a second predetermined value may indicate poor patient health and the need for immediate attention.

Figure 2:
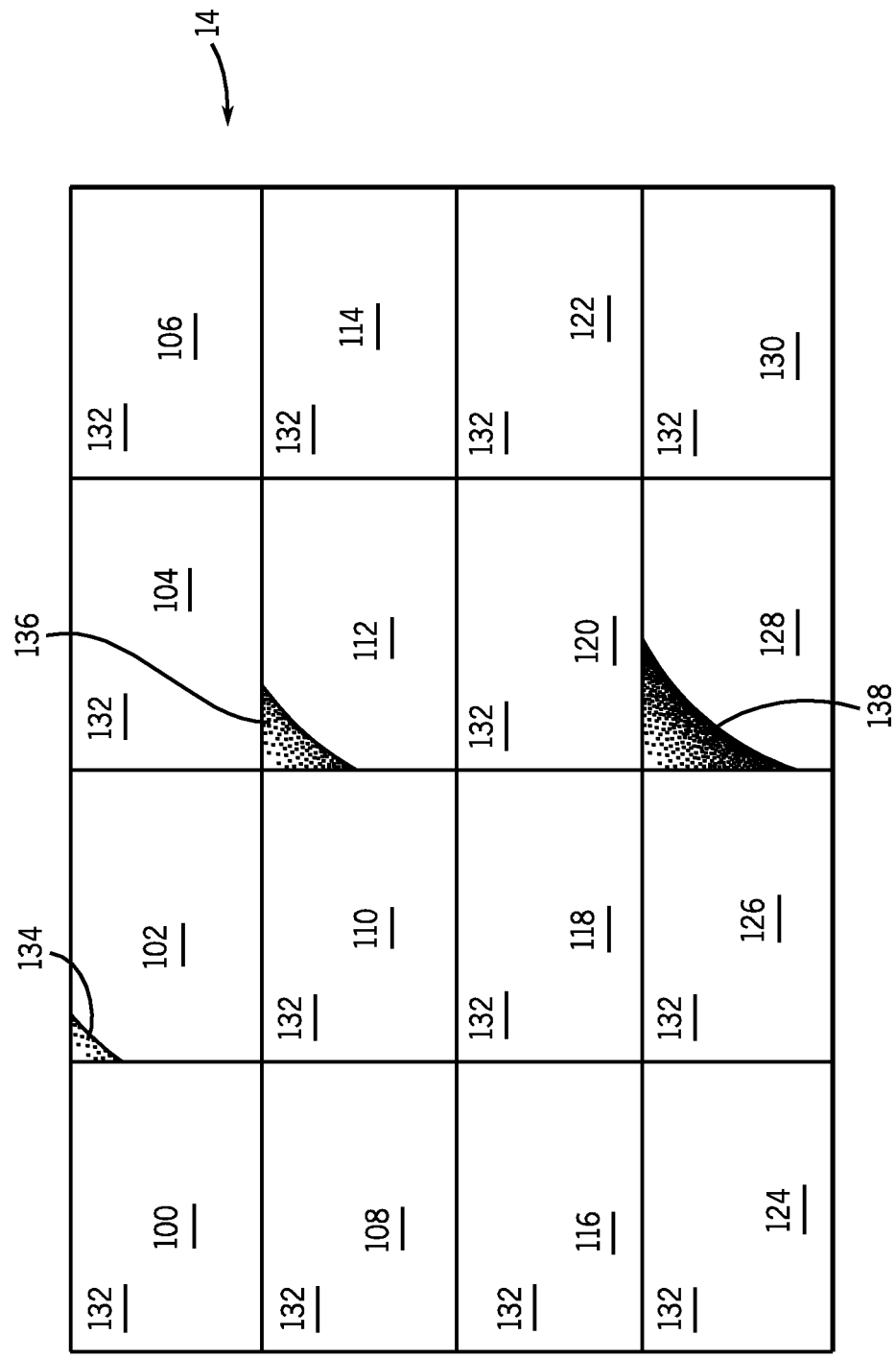
FIG. 2 is a schematic representation of a multi-patient display of the centralized patient monitoring system of FIG. 1 in accordance with an embodiment.

The computer 12 is also configured to generate a user interface for each monitored patient. According to one embodiment, each user interfaces comprises raw patient data and a visual health status indicator. A plurality of exemplary user interfaces 100-130 and health status indicators 132-138 are shown in FIG. 2. As will be described in more detail hereinafter, each health status indicator may be implemented to visually convey a wide range of patient health assessments such as, for example, the range extending from very good health to critically poor health.

The multi-patient display 14 is connected to the computer 12, and is configured to visually convey a user interface for each of a plurality of different patients. According to the embodiment depicted in FIG. 2, the multi-patient display 14 is partitioned into sixteen distinct regions that are each adapted to visually convey a different user interface such that the technician 16 can generally simultaneously monitor sixteen different patients with a single display. It should, however, be appreciated that alternate multi-patient display configurations may be envisioned.

Having described the operation of the centralized patient monitoring system 10 to assess patient health, the implementation of the multi-patient display 14 to visually convey such information will now be described in detail. Referring to FIG. 2, the multi-patient display 14 is shown in accordance with an embodiment. The multi-patient display 14 is configured to generally simultaneously display sixteen user interfaces 100-130 based on input from the computer 12. According to one embodiment, each user interface comprises raw patient data (not shown) and a visual health status indicator (e.g., status indicators 132-138). The raw patient data is generally provided to enable a more detailed analysis of each patient. The visual health status indicator is configured to enable an observer to quickly assess patient health from a more remote location than would otherwise be possible. The following will describe several different visual health status indicator embodiments in more detail.

The health status indicators 132-138 implement a color gradient adapted to convey patient health with a variable degree of color hue, saturation or intensity. For purposes of this disclosure, a color gradient should be defined as a spectrum or range of one or more colors. As an example, a red gradient may comprise a range extending from pure black (the complete absence of color) to bright red. Also for purposes of this disclosure, the term hue refers to a pure color (e.g., red, yellow, green, blue, etc.), the term saturation refers the level of color purity with respect to white, and the term intensity refers to the level of color purity with respect to black.

It should be appreciated that each color gradient may comprise numerous visually distinct degrees of saturation or intensity such that a correspondingly large range of patient health assessments (e.g., including but not limited to good health, moderate health, poor health and critical health) can be visually conveyed. It should also be appreciated that the color gradient enables a technician to quickly identify the patients in need of immediate attention, and to do so from a greater distance than would otherwise be possible.

For illustrative purposes, a more intense color is graphically depicted in FIG. 2 with a greater degree of stipple density. Accordingly, the health status indicator 132 without any stippling represents the absence of color (i.e., black), and the health status indicator 134 with a minimal range of stippling density represents a minimal range of color intensity. Similarly, the health status indicator 136 with a moderate range of stippling density represents a moderate range of color intensity, and the health status indicator 138 with the widest range of stippling density represents the maximum range of color intensity.

According to one embodiment, the color gradients may implement a single color hue to visually convey information pertaining to a given patient's health. As an example, the color gradients 132 may represent the absence of coloration in order to convey the fact that the monitored patients are in good health. Similarly, the color gradient 134 may represent a minimal color range from no intensity (i.e., black) to a red with very little intensity (i.e., dark red) adapted to convey moderate patient health. The color gradient 136 may represent a moderate color range from no intensity (i.e., black) to a mid range intensity red coloration adapted to convey poor patient health, and the color gradient 138 may represent the widest range of red coloration from no intensity (i.e., black) to high intensity red (i.e., bright red) adapted to convey critical patient health requiring immediate attention.

According to another embodiment, the color gradients may implement multiple color hues in order to convey both a patient health assessment and the specific type of patient data on which the health assessment is based. As an example, the color gradients 132-138 may implement varying degrees of red saturation or intensity to convey a patient health assessment based on heard rate, and varying degrees of blue saturation or intensity to convey a patient health assessment based on blood pressure.

Alternatively, the previously described color gradient may be replaced by or implemented in combination with other visual gradients such as a contrast gradient or an illumination gradient. As an example, a black and white display may implement a gray scale gradient with a variable degree of contrast or illumination to convey a patient health assessment. These alternative visual gradients may, for example, be implemented to ensure that colorblind technicians are able to readily and conveniently identify patient health.

According to another embodiment, the health status indicators 132-138 implement a visual gradient adapted to convey patient health based on shape and/or relative size. As an example, the health status indicator 134 covering only a relatively small percentage of the user interface 102 may represent moderate patient health. Similarly, the health status indicator 136 covering an intermediate percentage of the user interface 112 may represent poor patient health, and the health status indicator 138 covering a relatively large percentage of the user interface 128 may represent critical patient health requiring immediate attention.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A patient monitoring device comprising:
    a computer adapted to assess a current health status of a plurality of patients;
    a multi-patient display operatively connected to the computer and configured to simultaneously display raw patient data for each of the plurality of patients; and
    a health status indicator for each of the plurality of patients generated by the computer and shown on the multi-patient display with the raw patient data for each of the plurality of patients,
    said health status indicator comprising a visual gradient adapted to visually convey the assessed current health status for each of the plurality of patients by a variable range of color and size.

2. The system of claim 1, wherein said visual gradient includes a color gradient comprising a plurality of color hues with a variable range of color saturation and/or intensity.

3. The system of claim 1, wherein said visual gradient includes a contrast gradient configured to convey a patient health assessment with a variable degree of contrast.

4. The system of claim 1, wherein said visual gradient includes an illumination gradient configured to convey a patient health assessment with a variable degree of illumination.

5. The system of claim 1, wherein said health status indicator is configured to convey a patient health assessment with a variable shape.

6. A patient monitoring system comprising:
- a computer adapted to assess a current health status of a plurality of patients;
- a multi-patient display operatively connected to the computer to simultaneously display raw patient data for each of the plurality of patients; and
- a health status indicator generated by the computer for each of the plurality of patients and shown on the multi-patient display,
- said health status indicator comprising a color gradient configured to visually convey the assessed current health status for each of the plurality of patients with a variable range of color saturation and/or intensity and a variable size,
- wherein the health status indicator becomes larger in size to represent a poorer assessed health;
- wherein said multi-patient display is configured to simultaneously display the health status indicator for each of the plurality of patients along with the raw patient data for each of the plurality of patients.

7. The patient monitoring system of claim 6, wherein the multi-patient display is partitioned into a plurality of distinct regions that are each configured to display a separate health status indicator and separate raw patient data for each of the plurality of patients.

8. The patient monitoring system of claim 6, wherein said health status indicator is configured to convey a patient health assessment with a variable shape.

9. A method comprising:
- obtaining raw patient data from each of a plurality of patients;
- assessing the health of each of a plurality of patients based on the raw patient data using a computer;
- generating a health status indicator for each of said plurality of patients using the computer,
- said health status indicator configured to visually convey the patient health assessment with a color gradient consisting of a variable range of color saturation and/or intensity and a variable size,
- wherein the health status indicator transitions in color and size to represent a poorer assessed health; and
- generally simultaneously displaying the health status indicator for each of the plurality of patients along with the raw patient data for each of the plurality of patients.

10. The method of claim 9, wherein the health status indicator is configured to convey the patient health assessment with a variable shape.

11. The method of claim 9, wherein said step of generally simultaneously displaying the health status indicator includes implementing a multi-patient display.

* * * * *